(12) United States Patent
Kesten et al.

(10) Patent No.: US 9,198,559 B2
(45) Date of Patent: Dec. 1, 2015

(54) DEVICE AND METHOD TO DISPLAY THE ANGLE OF VIEW ENDOSCOPICALLY WHEN USING A MULTI-ANGLE ENDOSCOPE

(71) Applicant: Acclarent, Inc., Menlo Park, CA (US)

(72) Inventors: Randy J. Kesten, Mountain View, CA (US); John W. White, Menlo Park, CA (US)

(73) Assignee: Acclarent, Inc., Menlo Park, CA (US)

( * ) Notice: Subject to any disclaimer, the term of this patent is extended or adjusted under 35 U.S.C. 154(b) by 288 days.

(21) Appl. No.: 13/827,175

(22) Filed: Mar. 14, 2013

(65) Prior Publication Data

US 2014/0275785 A1  Sep. 18, 2014

(51) Int. Cl.
*A61B 1/06* (2006.01)
*A61B 1/00* (2006.01)
*A61B 1/04* (2006.01)

(52) U.S. Cl.
CPC ........... *A61B 1/00183* (2013.01); *A61B 1/0008* (2013.01); *A61B 1/00096* (2013.01)

(58) Field of Classification Search
CPC ............. A61B 1/00057; A61B 1/0008; A61B 1/00089; A61B 1/00096; A61B 1/00183
USPC ......... 600/173, 176, 104, 117, 127, 129, 170, 600/171, 174
See application file for complete search history.

(56) References Cited

U.S. PATENT DOCUMENTS

| | | | |
|---|---|---|---|
| 6,560,013 B1 | 5/2003 | Ramsbottom | |
| 6,626,828 B2 | 9/2003 | Dohi et al. | |
| 6,648,817 B2 | 11/2003 | Schara et al. | |
| 7,896,803 B2 | 3/2011 | Schara et al. | |
| 8,852,087 B2* | 10/2014 | Meyer | 600/173 |
| 2006/0129032 A1* | 6/2006 | Durell | 600/173 |
| 2007/0213590 A1* | 9/2007 | Squicciarini | 600/172 |
| 2009/0062658 A1* | 3/2009 | Dunki-Jacobs | 600/476 |
| 2010/0030031 A1 | 2/2010 | Goldfarb et al. | |
| 2010/0167248 A1* | 7/2010 | Ryan | 434/262 |
| 2011/0004057 A1 | 1/2011 | Goldfarb et al. | |
| 2011/0071536 A1* | 3/2011 | Kleiner | 606/94 |
| 2014/0300722 A1* | 10/2014 | Garcia | 348/77 |

\* cited by examiner

*Primary Examiner* — Anhtuan T Nguyen
*Assistant Examiner* — Timothy J Neal
(74) *Attorney, Agent, or Firm* — Frost Brown Todd LLC

(57) ABSTRACT

An endoscope comprises an elongate shaft assembly, a window, a viewing angle adjustment assembly, and an indicator feature. The window is located at the distal end of the shaft assembly. The shaft assembly is configured to transmit a view acquired through the window. The viewing angle adjustment assembly is operable to selectively change a viewing angle associated with the window. The indicator feature is positioned to be visible within a view acquired through the window. The indicator feature is configured to indicate the viewing angle associated with the window.

19 Claims, 7 Drawing Sheets

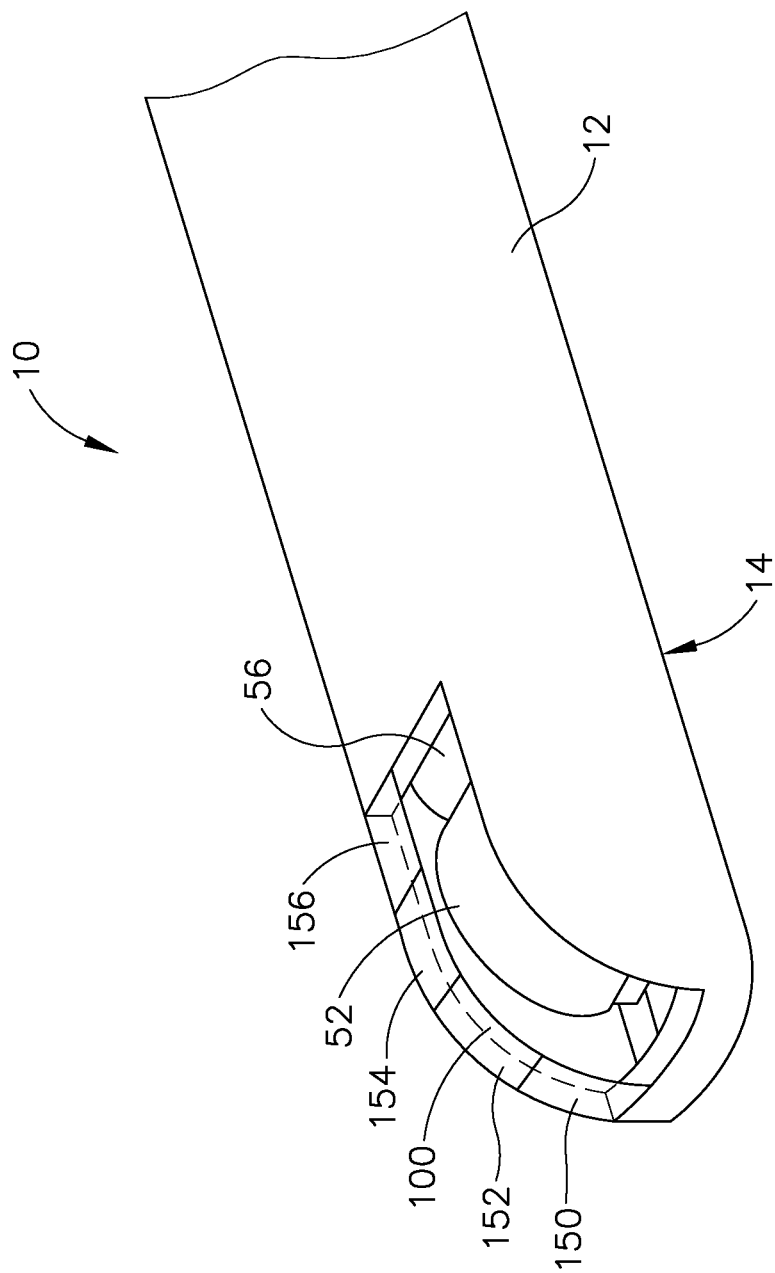

DEVICE AND METHOD TO DISPLAY THE ANGLE OF VIEW ENDOSCOPICALLY WHEN USING A MULTI-ANGLE ENDOSCOPE

BACKGROUND

An endoscope is a medical-imaging device that may be used to examine the interior of a hollow organ or cavity of the body. Endoscopes may be used to provide visualization for non-invasive treatment of conditions within the nasal cavity and nasopharynx (among other places). For instance, an example of such treatment in the nasal cavity is disclosed in U.S. Pat. Pub. No. 2011/0004057, entitled "Systems and Methods for Transnasal Dilation of Passageways in the Ear, Nose, or Throat," issued Feb. 4, 2010, the disclosure of which is incorporated by reference herein. An endoscope has an elongate body equipped with an imaging device for viewing of the treatment site within the patient. Some endoscopes are limited to a fixed viewing angle, however, a multi-angle endoscope is capable of a much broader range of viewing. A multi-angle endoscope is also capable of multiple viewing angles and rotation about the longitudinal axis of the elongate body. For instance, a multi-angle endoscope is disclosed in U.S. Pat. Pub. No. 2010/0030031, entitled "Swing Prism Endoscope," issued Feb. 4, 2010, the disclosure of which is also incorporated by reference herein.

With such a wide capability of viewing, it may be confusing for the operator of a multi-angle endoscope to keep track of the exact viewing angle. Some endoscopes may be equipped with a means of determining the viewing angle; however, the operator may be required to look away from the endoscopic view displayed on a monitor in order to determine the viewing angle of the instrument. An endoscope operator may wish to determine the exact viewing angle without having to look away from the endoscopic view displayed on the monitor.

While several medical devices have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 11 depicts a detailed perspective view of the distal end of the multi-angle endoscope of FIG. 1, showing an exemplary indicator feature formed by a series of color bars.

Figure 1:
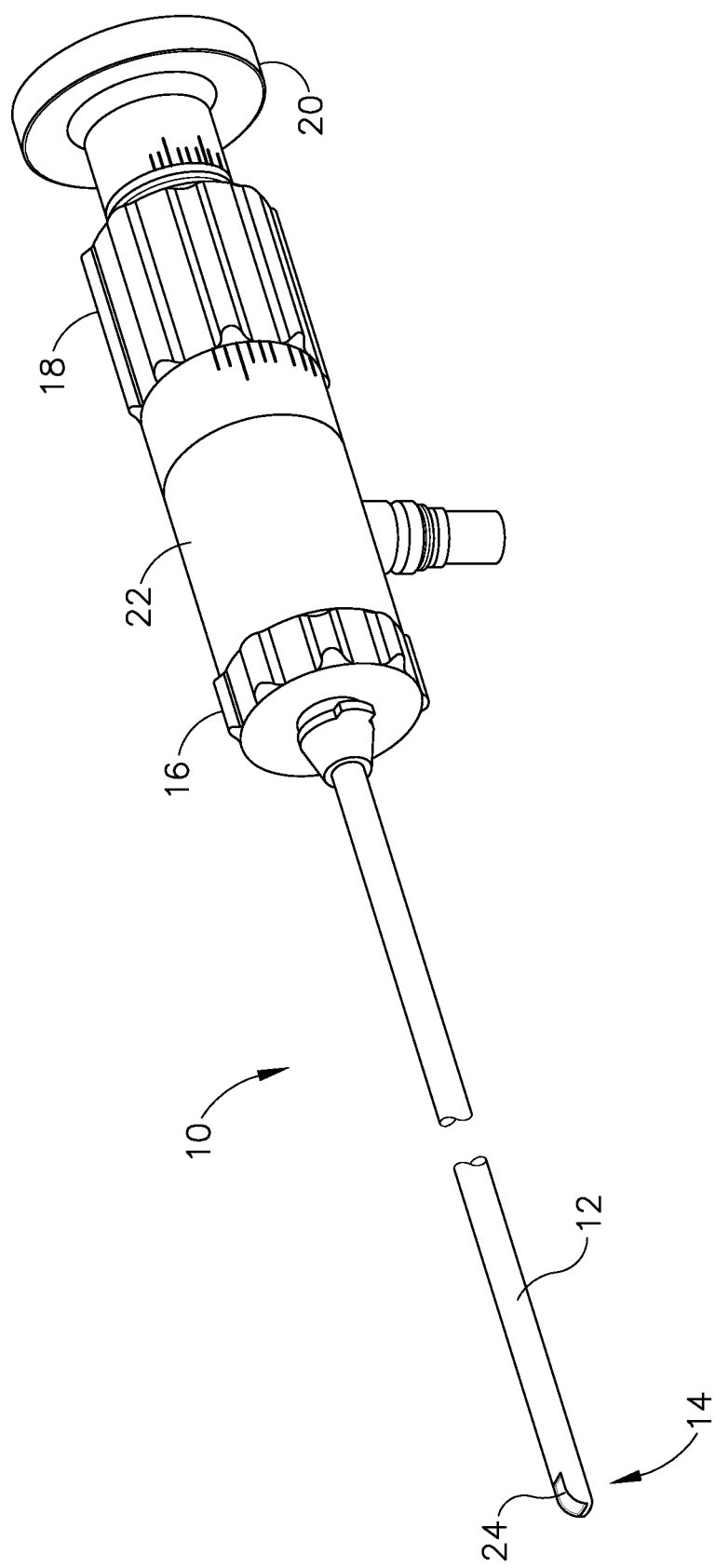
FIG. 1 depicts a perspective view of an exemplary multi-angle endoscope.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

As shown in FIG. 1, endoscope (10) of the present example comprises a body (22), a shaft (12), a directional control dial (16), an angle control dial (18), a distal portion (14), and an eyepiece (20). At least part of endoscope (10) is configured substantially in accordance with at least some of the teachings of U.S. Pat. Pub. No. 2010/0030031, entitled "Swing Prism Endoscope," published Feb. 4, 2010, the disclosure of which is incorporated by reference herein. Directional control dial (16) is operable to rotate shaft (12) relative to body (22), about the longitudinal axis (LA) defined by the shaft (12). Eyepiece (20) may be compatible with any standard endoscopic camera to communicate the images within the viewing field (200) to an external monitor (not shown).

Figure 2:
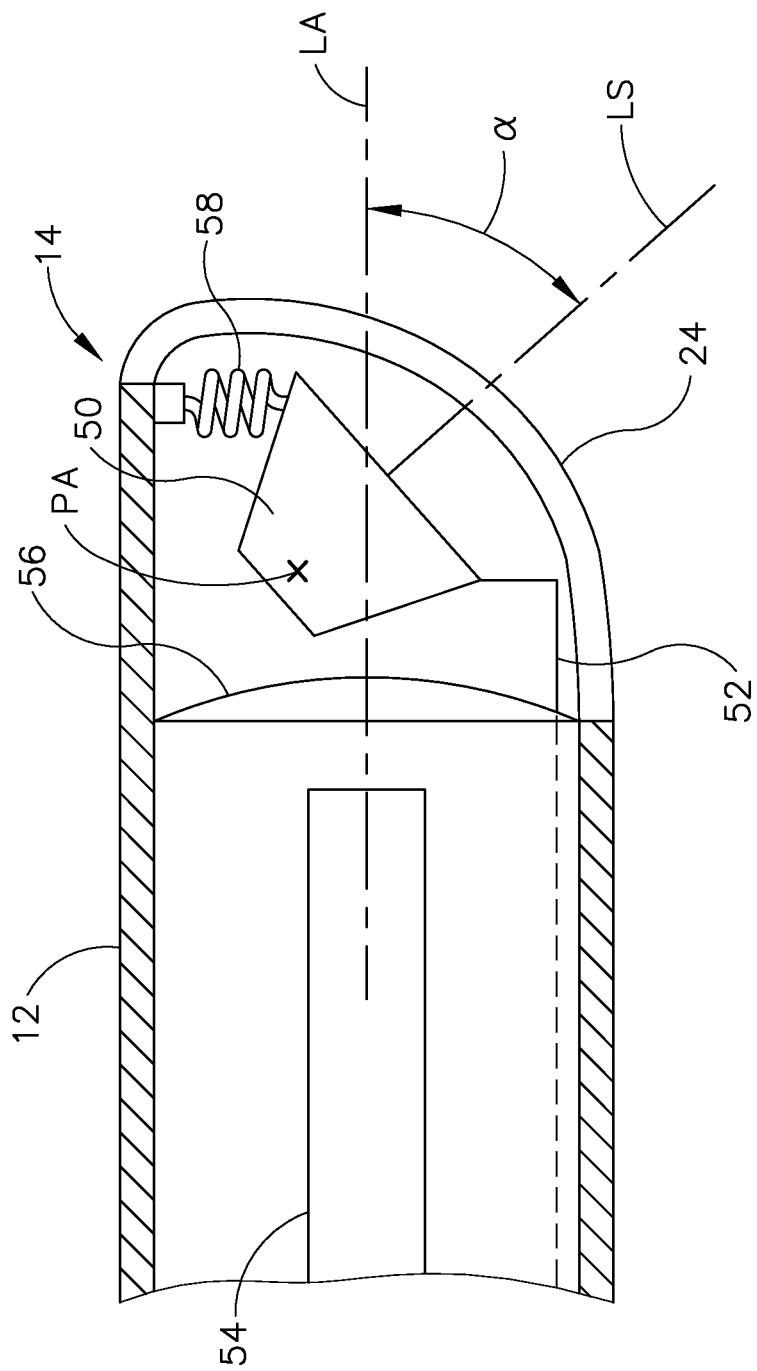
FIG. 2 depicts a cross-sectional side view of the distal end of the multi-angle endoscope of FIG. 1, with the window oriented downwardly.

As shown in FIG. 2, the distal portion (14) of shaft (12) in the present example comprises a swing prism (50), a translating actuator (52), and a self-focusing lens (56). The swing prism (50) is pivotally mounted within shaft (12) such that prism (50) pivots about a pivot axis (PA). The pivot axis (PA) extends transversely relative to the longitudinal axis (LA) of shaft (12). Translating actuator (52) is coupled with angle control dial (18) such that actuator (52) translates along a path that is parallel to the longitudinal axis (LA) when angle control dial (18) is rotated about the longitudinal axis (LA). By way of example only, a nut and lead screw assembly (not shown) may be used to convert rotary motion of angle control dial (18) into longitudinal motion of actuator (52). Actuator (52) may comprise any suitable structure, such as a push-pull cable, a rod, a beam, etc. Actuator (52) is operable to drive prism (50) to pivot about pivot axis (PA) when actuator (52) translates longitudinally. Thus, control dial (18) is rotatable to pivot prism (50). In the present example, prism (50) is coupled with a resilient member (58) that is anchored within shaft (12) and that resiliently biases prism (50) to an orientation where the line of sight (LS) is aligned with or at least parallel to longitudinal axis (LA). Of course, resilient member (58) may simply be omitted, if desired. It should also be understood that prism (50) may alternatively be driven in accordance with any of the teachings of U.S. Pat. Pub. No. 2010/0030031, the disclosure of which is incorporated by reference herein; and/or in any other suitable fashion.

Figure 3:
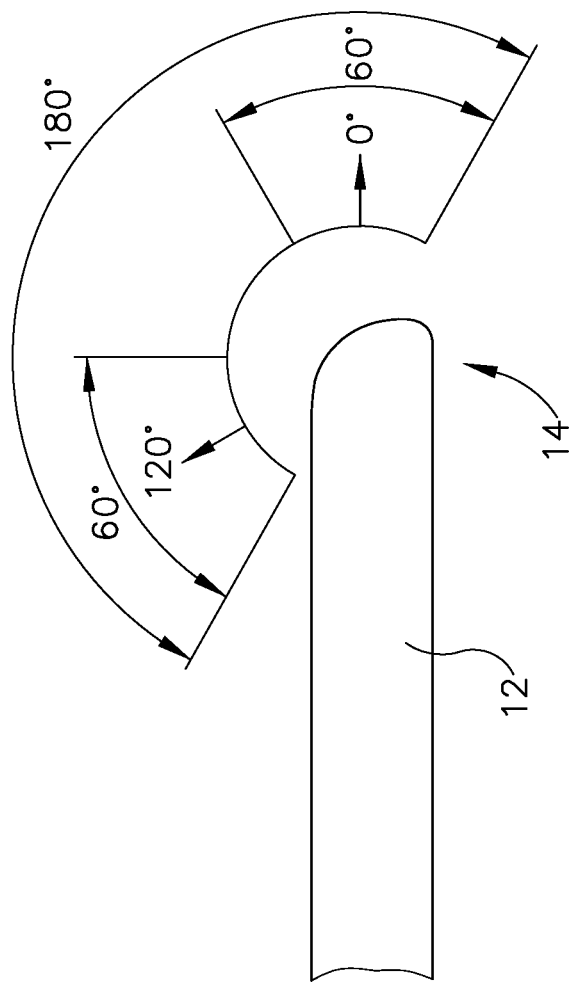
FIG. 3 depicts a detailed side view of the distal end of the multi-angle endoscope of FIG. 1, showing a range of viewing angles with the window oriented upwardly.

Prism (50) is configured to transmit a view from window (24) to self-focusing lens (56), with the view then being further transmitted through one or more rod lenses (54) located proximal to lens (56) to reach eyepiece (20). This view is based on a line of sight (LS) provided by prism (50), which changes as prism (50) pivots about pivot axis (PA). A viewing angle ($\alpha$) is defined between the line of sight (LS) provided by prism (50) and the longitudinal axis (LA) of shaft (12). The angle control dial (18) is operable to pan the viewing field (200) throughout a series of viewing angles ($\alpha$), as shown in FIGS. 2-3. The viewing angles ($\alpha$) of the present example range from 0° to 120°, through it should be understood that any other suitable range of viewing angles ($\alpha$) may be provided (e.g., from 10° to 90°). It should also be understood that swing prism (50) rotates with shaft (12) about the longitudinal axis (LA) of shaft (12), such that rotation of directional control dial (16) accomplishes rotation of swing prism (50) and the rest of shaft (12) about the longitudinal axis (LA) of shaft (12). Swing prism (50) is thus independently rotatable about two perpendicular axes (PA, LA).

Figure 4:
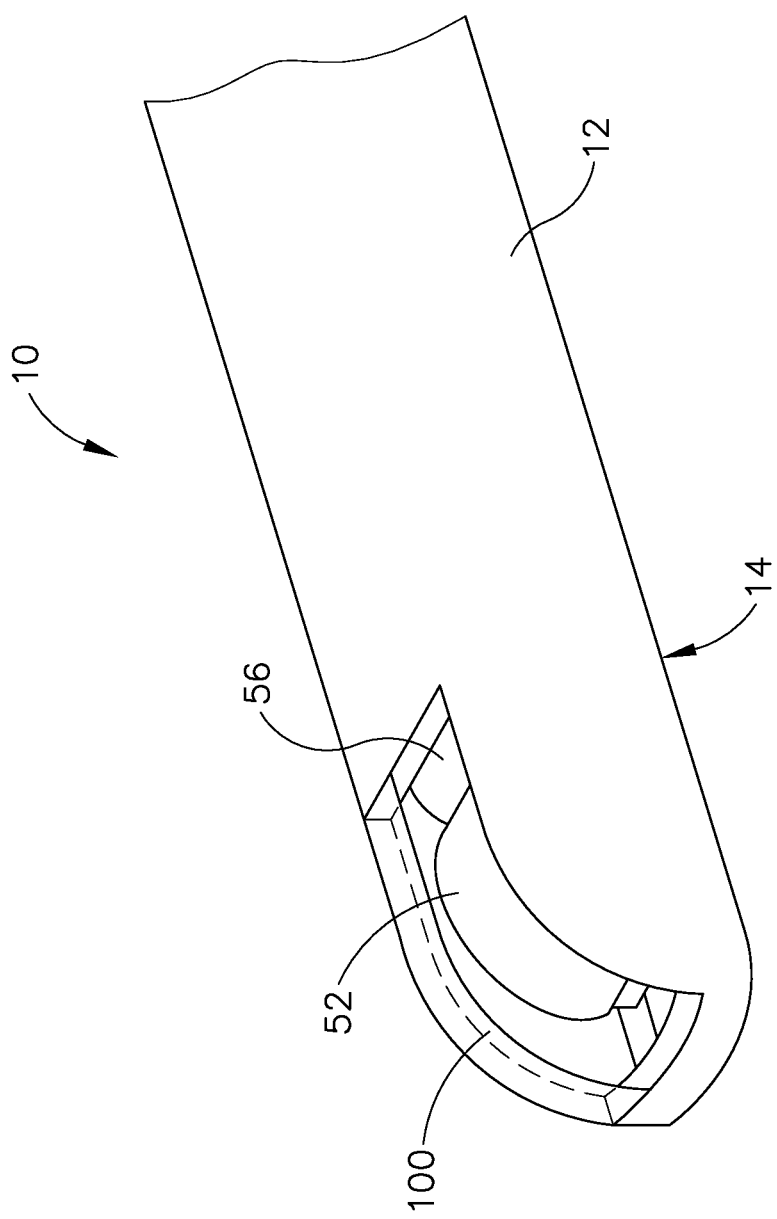
FIG. 4 depicts a detailed perspective view of the distal end of the multi-angle endoscope of FIG. 1, showing an exemplary indicator feature.

As shown in FIG. 4, window (24) extends along a curved path to accommodate the wide viewing angle ($\alpha$) range provided by swing prism (50). Window (24) of the present example comprises glass, but it should be understood that any other suitable material may be used (e.g., crystal, plastic, etc.). The rod lens (54) extends coaxially through the center of the shaft (12) to the eyepiece (20) and may transmit the image from window (24) and lens (56) to the eyepiece (20) or an external monitor (not shown). It may be desirable to utilize an indicator feature (100) at the distal portion (14) of the shaft (12) in order to display the viewing angle ($\alpha$) of the viewing field (200) through the eyepiece (20) and/or on an external monitor (not shown), as shown in FIGS. 4-10.

Figure 7:
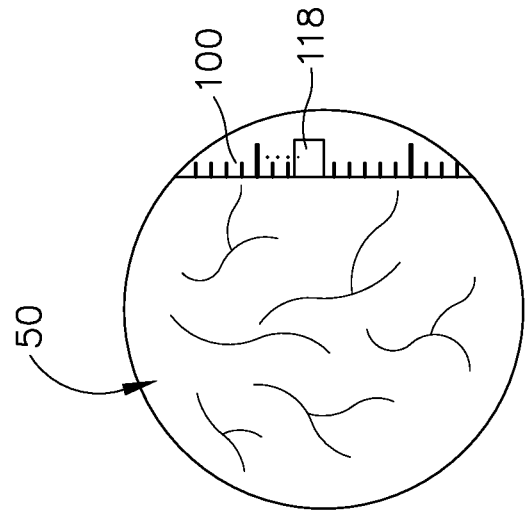
FIG. 7 depicts an endoscopic view of the exemplary indicator feature of FIG. 4 with the color coded indicators of FIG. 5, showing a viewing angle of 90°.
Figure 6:
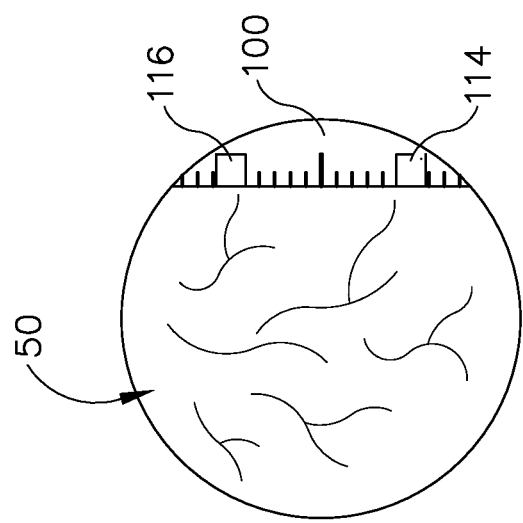
FIG. 6 depicts an endoscopic view of the exemplary indicator feature of FIG. 4 with the color coded indicators of FIG. 5, showing a viewing angle of 45°.
Figure 5:
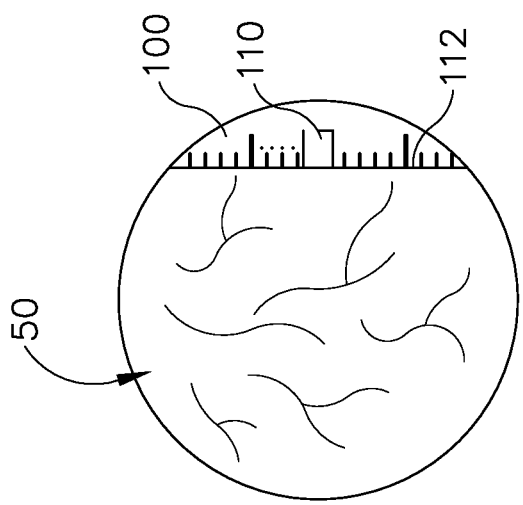
FIG. 5 depicts an endoscopic view of the exemplary indicator feature of FIG. 4 with an example of color coded indicators, showing a viewing angle of 10°.

As an example only, such an indicator feature (100) may comprise a series of indicators (110, 112, 114, 116, 118, 140) along the length of indicator feature (100), as shown in FIGS. 4-10. Indicator feature (100) of the present example comprises a curved extrusion at distal portion (14) of shaft (12). Such a curved shape will allow for indicator feature (100) to remain within the viewing field (200) of endoscope (10) as the operator pans viewing field (200) through a range of viewing angles ($\alpha$). Indicator feature (100) is positioned so that indicator feature (100) appears in the right most portion of viewing field (200), but may alternatively be positioned anywhere else within viewing field (200). Indicator feature (100) is secured to shaft (12) so that as shaft (12) is rotated by the operator about the longitudinal axis (LA) of shaft (12), indicator feature (100) rotates with shaft (12) and remains in viewing field (200) of endoscope (10). As the viewing angle ($\alpha$) is changed, different indicators (110, 112, 114, 116, 118, 140) may come into viewing field (200) and allow the operator to determine the viewing angle ($\alpha$) of the viewing field (200) without having to look away from eyepiece (20) or an external monitor (not shown). Indicators (110, 112, 114, 116, 118) may be color coded to quickly alert the operator of viewing angle ($\alpha$). For instance, the indicator at 10° (110) may be blue, the indicator at 20° (112) may be green, the indicator at 40° (114) may be yellow, the indicator at 50° (110) may be orange, and the indicator at 90° (110) may be red, as shown in FIGS. 5, 6, and 7. The indicators (110, 112, 114, 116, 118, 140) may be etched, lasered, painted, stenciled, or otherwise created on or within the window (24) through any other appropriate method. Alternatively, the indicator feature (100) may be made from metal, plastic, or any other suitable materials that are secured to or near the inner or outer surface of the window (24) in any suitable fashion.

Figure 10:
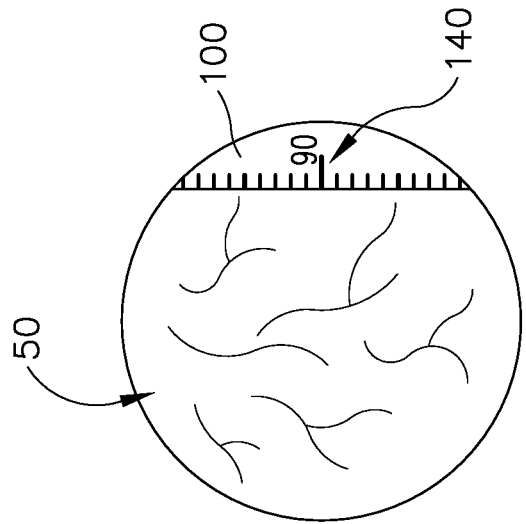
FIG. 10 depicts an endoscopic view of the exemplary indicator feature of FIG. 4 with the numerical indicators of FIG. 8, showing a viewing angle of 90°.
Figure 9:
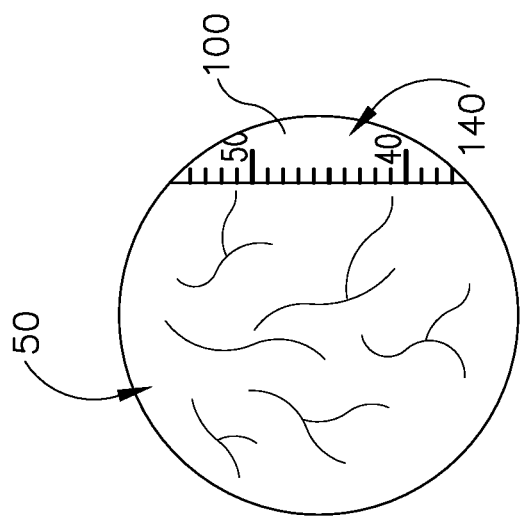
FIG. 9 depicts an endoscopic view of the exemplary indicator feature of FIG. 4 with the numerical indicators of FIG. 8, showing a viewing angle of 45°.
Figure 8:
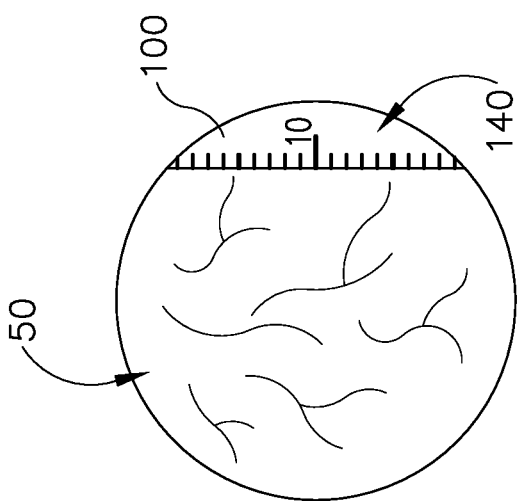
FIG. 8 depicts an endoscopic view of the exemplary indicator feature of FIG. 4 with an example of numerical indicators, showing a viewing angle of 10°.

As another merely illustrative example, indicators (140) may display the numerical value of the viewing angle ($\alpha$), as shown in FIGS. 8, 9, and 10. As yet another example only, indicators (not shown) may include a lettering scheme that allows the operator to determine the viewing angle ($\alpha$).

FIG. 11 shows yet another merely exemplary form of indicator (100), formed by a series of adjacent color bars (150, 152, 154, 156). Color bars (150, 152, 154, 156) of the present example include a blue color bar (150), a green color bar (152), a yellow color bar (154), and a red color bar (156). Of course, any other suitable number of color bars, arrangement of color bars, and selection of colors may be used. It should be understood that the use of color bars (150, 152, 154, 156) may facilitate viewing and interpretation of indicator (100) when indicator (100) is out of focus. For instance, due to the depth of field provided by the optics of endoscope (10), lens (56) and the rest of the optics of endoscope (10) may be focused on an anatomical structure of the patient during use of endoscope (10), and indicator (100) may be too far outside the depth of field to be viewed simultaneously with the anatomical structure with much sharpness. An indicator (100) in the form of color bars (150, 152, 154, 156) may nevertheless be sufficiently discernible even when color bars (150, 152, 154, 156) are significantly out of focus, enabling the operator to keep the anatomical structure in focus while simultaneously reading indicator (100). Other suitable forms that indicator (100) may take will be apparent to those of ordinary skill in the art in view of the teachings herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An endoscope comprising:
   (a) an elongate shaft assembly having a proximal end and a distal end, wherein at least a portion of the elongate shaft assembly is sized to fit within an anatomical passageway of a patient;
   (b) a window located at the distal end of the shaft assembly, wherein the shaft assembly is configured to transmit a view acquired through the window;
   (c) a viewing angle adjustment assembly operable to selectively change a viewing angle associated with the window; and
   (d) an indicator feature positioned to be visible within a view acquired through the window, wherein the indicator feature is positioned along a side region of the window, wherein the indicator feature is configured to indicate the viewing angle associated with the window.

2. The endoscope of claim 1, wherein the indicator feature is defined by an extrusion along a side of the window.

3. The endoscope of claim 1, wherein the window comprises glass.

4. The endoscope of claim 3, wherein the indicator feature is positioned on the glass of the window.

5. The endoscope of claim 1, wherein the indicator feature is disposed on an inner surface of the window.

6. The endoscope of claim 1, wherein the indicator feature is etched, lasered, or stenciled on the window.

7. The endoscope of claim 1, wherein the indicator feature comprises a sticker.

8. The endoscope of claim 1, wherein the indicator feature comprises at least one color coded indicator mark.

9. The endoscope of claim 8, wherein the indicator feature comprises a color strip formed by a series of color bars, wherein the colors of the color bars change from one end of the color strip to another end of the color strip.

10. The endoscope of claim 9, wherein color bars comprise:
    (i) a blue color bar associated with a substantially longitudinal viewing angle, and
    (ii) a red color bar associated with a substantially transverse viewing angle.

11. The endoscope of claim 1, wherein the indicator is configured to be discernable while being out of focus.

12. The endoscope of claim 1, wherein the indicator feature comprises at least one numerical indicator mark.

13. The endoscope of claim 1, wherein the viewing angle adjustment assembly comprises a rotatable prism disposed in the shaft assembly at the distal end of the shaft assembly, wherein the rotatable prism is rotatable to selectively change the viewing angle associated with the window.

14. The endoscope of claim 13, wherein the shaft assembly defines a longitudinal axis, wherein the rotatable prism is rotatable about an axis that is transverse to the longitudinal axis of the shaft assembly.

15. The endoscope of claim 13, wherein the window is fixed relative to the shaft assembly, such that the rotatable prism is rotatable relative to the shaft assembly and relative to the window.

16. The endoscope of claim 1, wherein the shaft assembly is rigid.

17. The endoscope of claim 1, wherein the shaft assembly defines a longitudinal axis, wherein the shaft assembly is rotatable about the longitudinal axis of the shaft assembly.

18. An endoscope comprising:
    (a) a shaft assembly having a proximal end and a distal end;
    (b) a window positioned at the distal end of the shaft assembly;
    (c) a pivotable prism disposed in the shaft assembly near the distal end of the shaft assembly, wherein the pivotable prism is pivotable within the shaft assembly throughout a range of viewing angles to change an angle of view through the window;
    (d) a lens disposed in the shaft assembly, wherein the lens is configured to focus a view acquired through the window and prism; and
    (e) an indicator feature positioned to be visible within the view acquired through the window, wherein the indicator extends completely the length of the viewing window such that the indicator is configured to continuously indicate a viewing angle associated with the view acquired through the window and prism throughout the range of viewing angles of the pivotable prism.

19. An endoscope comprising:
(a) a shaft assembly having a proximal end and a distal end, wherein the shaft assembly defines a longitudinal axis, wherein the shaft assembly is rotatable about the longitudinal axis;
(b) a window positioned at the distal end of the shaft assembly;
(c) a rotatable prism disposed in the shaft assembly near the distal end of the shaft assembly, wherein the rotatable prism is rotatable within the shaft assembly about an axis transverse to the longitudinal axis of the shaft assembly to change an angle of view through the window;
(d) a lens disposed in the shaft assembly, wherein the lens is configured to focus a view acquired through the window and prism; and
(e) an angle indicating feature positioned on or adjacent to the window.

* * * * *